United States Patent [19]

Takayama et al.

[11] Patent Number: 5,003,991
[45] Date of Patent: Apr. 2, 1991

[54] HYPERTHERMIA APPARATUS

[75] Inventors: Syuichi Takayama; Takashi Tsukaya; Yasuhiro Ueda; Shinji Hatta; Masashi Abe, all of Tokyo, Japan

[73] Assignee: Olympus Optical Co., Ltd., Japan

[21] Appl. No.: 172,554

[22] Filed: Mar. 24, 1988

[30] Foreign Application Priority Data

| Mar. 31, 1987 | [JP] | Japan | 62-76460 |
| Mar. 31, 1987 | [JP] | Japan | 62-76461 |
| Mar. 31, 1987 | [JP] | Japan | 62-76463 |
| Apr. 8, 1987 | [JP] | Japan | 62-84667 |
| Apr. 17, 1987 | [JP] | Japan | 62-94482 |

[51] Int. Cl.$^5$ ............................................. A61N 1/32
[52] U.S. Cl. ................................. 128/784; 128/401; 128/422; 128/804
[58] Field of Search ................. 128/784–786, 128/788, 804, 422, 401, 798, 799

[56] References Cited

U.S. PATENT DOCUMENTS

| 4,140,130 | 2/1979 | Storm, III | 128/804 |
| 4,285,346 | 8/1981 | Armitage | 128/804 |
| 4,676,258 | 6/1987 | Inokuchi et al. | 128/804 |
| 4,846,196 | 7/1989 | Wiksell et al. | 128/784 |

Primary Examiner—Lee S. Cohen
Attorney, Agent, or Firm—Parkhurst, Wendel & Rossi

[57] ABSTRACT

A hyperthermia apparatus for effecting the thermotherapy by heating a cancer locally including two outside-body electrodes to be arranged on an outer surface of a patient's body, an inside-body electrode to be inserted into a cavity of the patient's body, a high frequency power supply circuit for generating a high frequency power, and a switch connected between the high frequency power supply circuit and the electrodes for selectively supplying the high frequency power to two electrodes so that the cancer can be locally heated to a desired high temperature. At each electrode there are provided balloons through which temperature controlled liquid mediums are circulated to prevent portions of the body near the electrodes from being heated to undesired high temperatures. The liquid mediums circulated through the balloons are electrically isolated from each other completely.

11 Claims, 10 Drawing Sheets

FIG_7

FIG_9
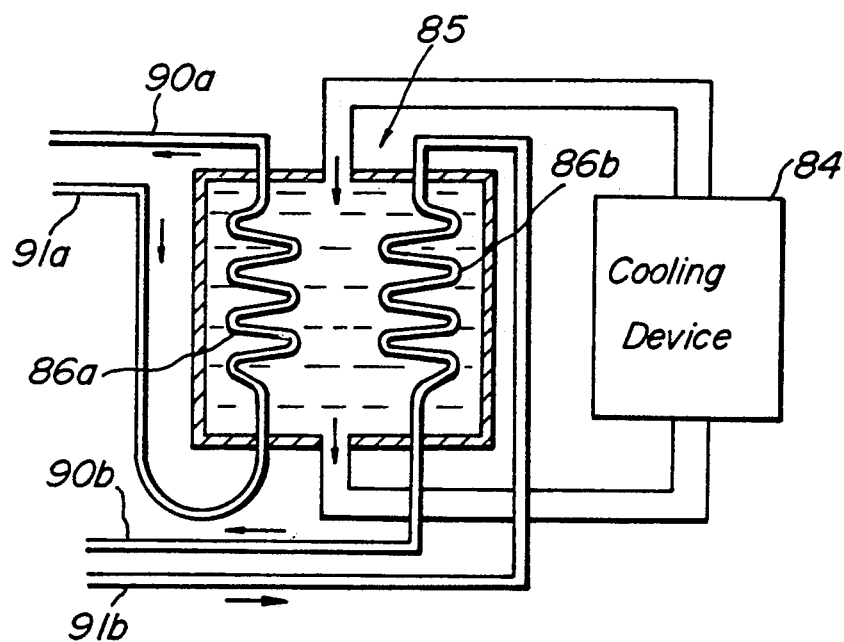
FIG_10
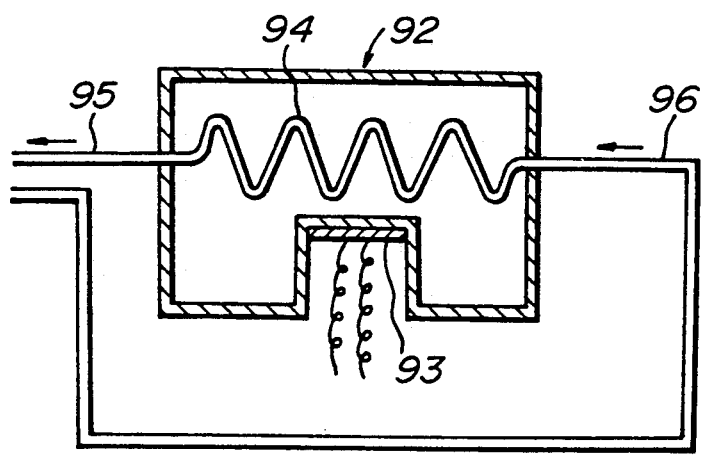

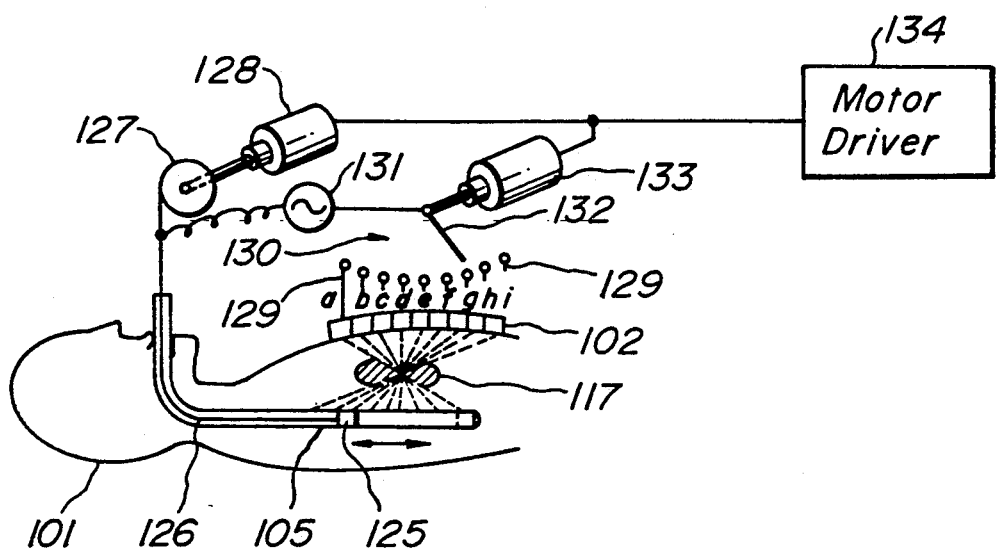
FIG_12

HYPERTHERMIA APPARATUS

BACKGROUND OF THE INVENTION

Field of the Invention and Related Art Statement

The present invention relates to a hyperthermia apparatus for use in a thermotherapy in which malignant body tissues, particularly cancer tissues are necrosed by selectively heating them with electric fields at high frequencies.

The hyperthermia apparatus has been developed to necrose cancer tissues by heating them above a temperature higher than 45°~43° C. due to the fact that the cancer tissues are liable to be damaged by heat rather than normal tissues. There have been proposed various types of hyperthermia apparatuses.

For instance, in Japanese Patent Publication Kokai No. 59-135,066, there is disclosed a hyperthermia device comprising a single inside-body electrode and a single outside-body electrode. This type of hyperthermia apparatus has been manufactured and sold by Kureha Kagaku Kogyo Co., Ltd. in Japan under the trade name of Endoradiotherm 100A. In U.S. Pat. No. 1,350,168 and Japanese Utility Model Publication No. 58-8,254, there is described another type of hyperthermia apparatus comprising a plurality of outside-body electrodes which are arranged around the patient's body and a switching means for selectively using a pair of electrodes which are faced to each other via the body of the patient.

FIG. 1 is a schematic view illustrating the known hyperthermia apparatus disclosed in said Japanese Patent Publication Kokai No. 59-135,066. In this known hyperthermia apparatus an inside-body electrode 4 is inserted into a cavity 2 of a patient's body 1 and an outside-body electrode 5 is placed on the outer surface of the body such that these electrodes are faced to each other via a cancer 3. Across the inside-body electrode 4 and outside-body electrode 5 is applied an RF electric power from an RF oscillator 6 to generate an electric field at a high frequency within the patient's body 1, and then a portion of the body 1 between these electrodes is heated by the electromagnetic induction. The electrode 4 is inserted into the cavity 2, so that its surface area is much smaller than that of the electrode 5. Therefore, the density of the high frequency electric field becomes higher toward the inside-body electrode 4.

FIG. 2 is a schematic view illustrating another known hyperthermia apparatus including a plurality of outside-body electrodes. This type of apparatus is disclosed in the above mentioned Japanese Utility Model Publication No. 58-8,254. In this known hyperthermia apparatus, on an outer surface of a patient's body 1, there are arranged outside-body electrodes 7 and 8 such that a cancer 3 is sandwiched by these electrodes. Then, an RF electric power is applied across the electrodes 7 and 8 from an RF oscillator 9 to generate an electric field of high frequency so that a portion of the body 1 between the electrodes 7 and 8 is selectively heated by the electromagnetic induction.

In the known hyperthermia apparatus illustrated in FIG. 1, since the density of the higy frequency electric field is increased toward the inside-body electrode 4, the body is preferably heated locally. However, this local heating has a demerit in some applications and a part of the cancer 3 may not be heated due to an error in the positioning of the electrodes or due to the size of the cancer 3. For instance, in the esophagus where a long cancer is liable to from in a longitudinal direction of the esophagus, it is practically impossible to heat the whole cancer to a predetermined temperature, and a part of the cancer is therefore not sufficiently heated. Then, this part of the cancer may not be necrosed, and grows. Moreover, since there is provided only one outside-body electrode 4, when a plurality of cancers are existent around the patent body 1, it is necessary to rearrange the electrode 4, which makes the operation cumbersome.

In the known hyperthermia apparatus depicted in FIG. 2, the outside-body electrodes 7 and 8 may have a relatively large surface area, so that the cancer 3 having a large area can be heated to the effective temperature. However, the high frequency electric field is spread widely between the large electrodes, and thus the normal tissues surrounding the cancer tissues might be heated to a higher temperature. Therefore, the hyperthermia apparatus could not be used for a long time period. As is well known in the art, the effect of the thermotherapy depends on not only the temperatures to which the tissues are heated, but also upon the time period for which the tissues are held at such temperatures. In this known hyperthermia apparatus, in order not to heat the normal tissues excessively, there is provided a cooling means of a large scale at the electrode. This results in the whole electrode becoming complicated in construction and large in size.

In the known hyperthermia apparatus described in the above mentioned U.S. Pat. No. 4,350,168, there is provided a cooling means beside an electrode in order to cool the patient body near the electrode. The coolimg means includes a balloon and a device for circulating cooling water through the balloon.

In the U.S. Pat. No. 4,350,168, there is also shown another hyperthermia apparatus including three pairs of outside-body electrodes and high frequency powers having mutual phase difference of 123° being applied to respective pairs of electrodes. In this known appartus, three pairs of electrodes would operate just like a single pair of electrodes, so that the normal tissues near the electrodes might be heated to undesired high temperatures. Further, if more than three pairs of electrodes are provided the mutual phase difference of the driving signals becomes smaller, and a high frequency current might flow into adjacent electrodes so that all the electrodes would operate as a single pair of electrodes.

In Japanese Patent Publication Kokai 60-119,962, there is disclosed inside-body and outside-body applicators each including an electrode, a balloon surrounding the electrode and a device for circulating a cooling medium through the balloon. By using such applicators, the normal tissues can be prevented from being heated excessively. In this known hyperthermia apparatus, the cooling medium circulating device is commonly used for the balloons of both the inside-body and outside-body applicators. In this apparatus, in order to prevent the electrodes from being short-circuited, the cooling medium has to be made of an electrically insulating substance. However, if the electrode is surrounded by the insulating medium, the impedance between the electrodes is increased and the high frequency electric field may not be produced in the living body at a high efficiency and the tissues may not be heated to the desired high temperature. Therefore, an electrically conductive substance has to be used as the cooling medium, and thus there are provided separate devices for circulating the cooling mediums through respective balloons in order to avoid the short-circuiting. However, in the known hyperthermia apparatus these devices are not completely isolated from each other. For example, even if pipes connected to the balloons and pumps for circulating the cooling mediums through the balloons are provided separately, when the pumps and cooling devices are connected commonly to a power supply line, the cooling mediums might be electrically connected to each other by means of the power supply line, and the patient may not be protected against danger.

In Japanese Patent Publication No. 56-38,230, there is described still another known hyperthermia apparatus. In this known apparatus, there is arranged an automatic impedance matching circuit for matching an output impedance of a high frequency oscillator and an input impedance of a load circuit including electrodes to which is supplied high frequency electric power from the oscillator and the living body, so that the high frequency electric field can be generated efficiently in the living body.

Howwver, in such a known hyperthermia apparatus, there is not provided a protection means for the impedance mismatching at the start of applying the high frequency electric power, so that the electric device might be damaged by the high electric power reflected from the load due to the mismatching.

Moreover, in the known hyperthermia apparatus in which the electrodes are selectively switched into and out of the circuit, after switching the electrodes, the high frequency electric power is adjusted to have a desired amplitude and then is applied to the electrodes. However, the impedance of the load including the selected electrodes might vary due to various factors such as condition of the living body, contact condition of the electrodes to the body and connecting condition of the electrodes to connectors. Therefore, the impedance mismatching might be produced and the instrument might be damaged by the reflected high power. Further, the patient might be subjected to an electrical shock.

SUMMARY OF THE INVENTION

A primary object of the present invention is to provide a novel and useful hyperthermia apparatus in which malignant tissues can be wholly heated to a desired temperature for a desired time period, while normal tissues can be effectively prevented from being heated excessively.

It is another object of the invention to provide a hyperthermia apparatus which can be utilized in a highly safe manner by separating electrically cooling mediums each being circulated through balloons surrounding respective electrodes in a complete manner.

It is still another object of the invention to provide a hyperthermia apparatus which does not require a complicated means for cooling an electrode.

It is still another object of the present invention to provide a hyperthermia apparatus in which the damage to the apparatus and living body due to the impedance mismatching when a high frequency electric power is applied to electrodes or electrodes are selectively switched into a circuit.

In order to attain the above object, according to the invention, a hyperthermia apparatus comprises inside-body electrode means including at least one inside-body electrode to be inserted into a cavity of a living body;

outside-body electrode means including at least two outside-body electrodes to be applied on an outer surface of the living body;

selection means for selecting two electrodes including at least one outside-body electrode among said outside-body and inside-body electrodes; and power source means for applying a high frequency electric power across the two electrodes selected by said selection means to heat a cancer in the living body to a desired temperature.

In a preferred embodiment of the hyperthermia apparatus according to the invention, each of said electrodes is formed as an applicator including a balloon which surrounds the electrode, and there are provided devices for circulating cooling mediums through respective balloons, said devices are electrically isolated from each other in a complete fashion. In such a hyperthermia apparatus, although use are made of electrically conductive cooling mediums circulating through respective balloons, these mediums are completely isolated from each other, any accident of short-circuiting can be removed to improve safety. Moreover, various electrical instruments of the cooling means may be connected commonly to the same power supply line without causing any trouble, so that the consturction becomes much simpler.

In another preferred embodiment of the hyperthermia apparatus according to the invention, inside-body electrodes and/or outside-body electrodes are divided into plurality of sections and a high frequency electric power is successively supplied to these electrode sections at a given period. Then the electrode sections can be effectively prevented from being locally heated to a high temperature and the heat can be efficiently radiated or diffused, so that normal tissues are effectively protected against the damage.

In still another preferred embodiment of the hyperthermia apparatus according to the invention, there are provided an automatic impedance matching circuit for matching an output impedance of the high frequency electric power supply means with respect to an impedance of a load, and a control circuit for controlling the high frequency electric power supplying means such that the output power of the supplying means is set to a low level at the start of the power supply and is changed to a desired high level after the impedance matching has been substantially attained by said automatic impedance matching circuit. In this embodiment, before connecting electrodes selected by said selection means to the high frequency power supplying means, the output level of the power supplying means is changed to a low or zero level, and after the impedance matching is performed by the impedance matching circuit, the output level of the power supplying means is changed to the desired high level.

BRIEF DESCRIPTION OF THE DRAWINGS

FIGS. 9 and 10 are cross sectional views showing two embodiments of a heat exchanger of the apparatus shown in FIG. 8;

FIG. 12 is a schematic view depicting a modified embodiment of the hyperthermia apparatus of FIG. 11.

DESCRIPTION OF THE PREFERRED EMBODIMENTS

Figure 1:
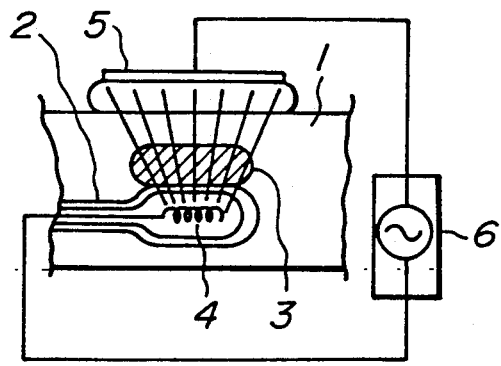
FIG. 1 is a schematic view showing a known hyperthermia apparatus including an outside-body electrode and an inside-body electrode.
Figure 2:
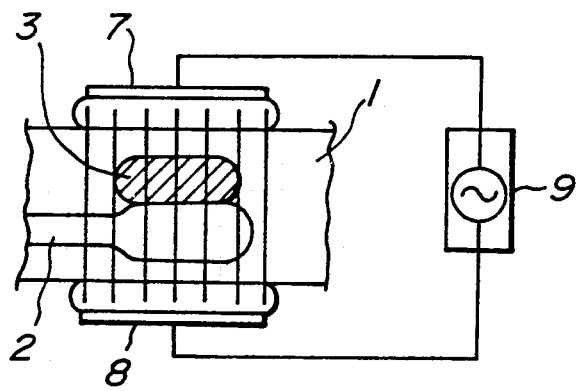
FIG. 2 is a schematic view illustrating a known hyperthermia apparatus comprising two outside-body electrodes.
Figure 3:
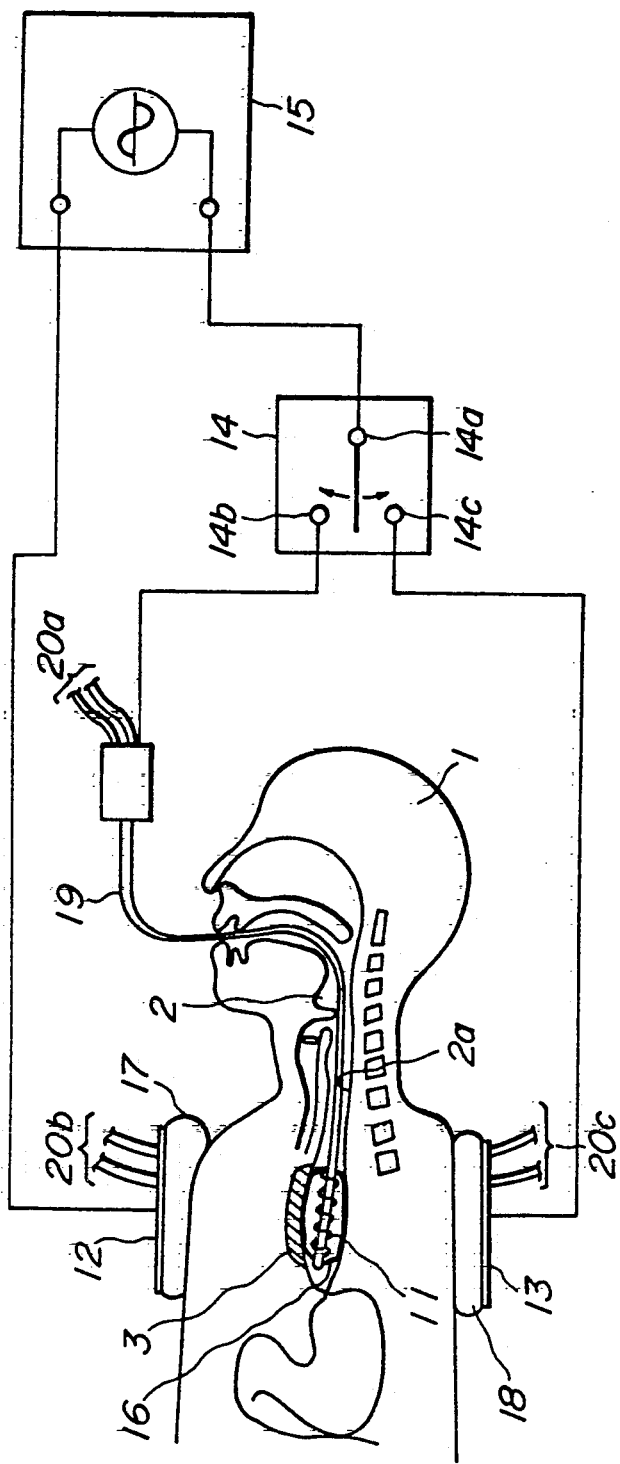
FIG. 3 is a schematic view depicting the construction of an embodiment of the hyperthermia apparatus according to the invention.

FIG. 3 is a schematic view showing an embodiment of the hyperthermia apparatus according to the invention. In the present embodiment, there are provided a single inside-body electrode 11 (hereinafter referred to as first electrode), two outside-body electrodes 12 and 13 (referred to as second and third electrodes, respectively), and a selection switch 14. The selection switch 14 serves to connect a first combination of the first and second electrodes 11 and 12 or a second combination of the second and third electrodes 12 and 13 to a high frequency power supply source 15 so that an electric field of a Radio Frequency can be applied across the electrodes 11 and 12 or the electrodes 12 and 13.

The first electrode 11 is arranged at a distal end of a flexible thin tube 19 and is inserted into a cavity 2 of a patient's body 1 at such a position that the first electrode is faced to a cancer 3. In FIG. 3, the apparatus is utilized to destroy the cancer 3 formed in an esophagus 2a. The first electrode 11 is surrounded by a balloon 16. Through the balloon 16, an electrically conductive liquid medium such as physiological saline solution is circulated via tubes 20a inserted into the insertion tube 19 and a heat exchanger (not shown to) heat or cool a cavity wall against which the balloon 16 is urged.

The second electrode 12 is placed on a front surface of the body 1 such that it is faced to the first electrode 11 via the cancer 3. Further, the third electrode 13 is arranged on a rear surface of the body 1 at such a position that it is faced to the second electrode 12. Similar to the first electrode 11, the second and third electrodes 12 and 13 are surrounded by balloons 17 and 18, respectively. An electrically conductive liquid medium such as physiological saline solution is circulated through the balloons 17 and 18 by means of tubes 20b and 20c and a heat exchanger (not shown), so that parts of the body 1 contacting the balloons 17 and 18 are cooled. It should be noted that the heating or cooling system for the first electrode 11 and the cooling systems for the second and third electrodes 12 and 13 are electrically isolated from each other as will be explained later.

The RF power supply device 15 has two output termianls, one of which is directly connected to the second electrode 12 and the other of which is connected to a switching contact 14a of the selection switch 14 whose fixed contacts 14b and 14c are connected to the first and third electrodes 11 and 13, respectively. Therefore, in the present embodiment, the second outside-body electrode 12 is always connected to the RF power supply device 15.

When a switching arm of the switch 14 is connected to the fixed contact 14b, the first and second electrodes 11 and 12 are selected and the RF electric field is selectively generated across these electrodes. When the switching arm of the switch 14 is changed to the fixed contact 14c, the second and third electrodes 12 and 13 are selected and the RF electric field is produced thereacross. Therefore, by changing the switching arm periodically, the first pair of electrodes 11, 12 and the second pair of electrodes 12, 13 are alternatively selected. The switching arm of the switch 14 may be driven manually or automatically in accordance with a program which has been set on the basis of the dimension and position of the cancer 3. Further, the application of the RF electric power to the electrodes can be automatically controlled by means of temperature sensors such as thermo-couples arranged on the outer surfaces of the balloons 16 to 18 in such a manner that when sensed temperatures exceed predetermined temperatures, the application of the RF power is interrupted until the sensed temperatures become lower than the predetermined temperatures. In this manner, the cancer 3 can be maintained substantially at the desired temperature.

Figure 4:
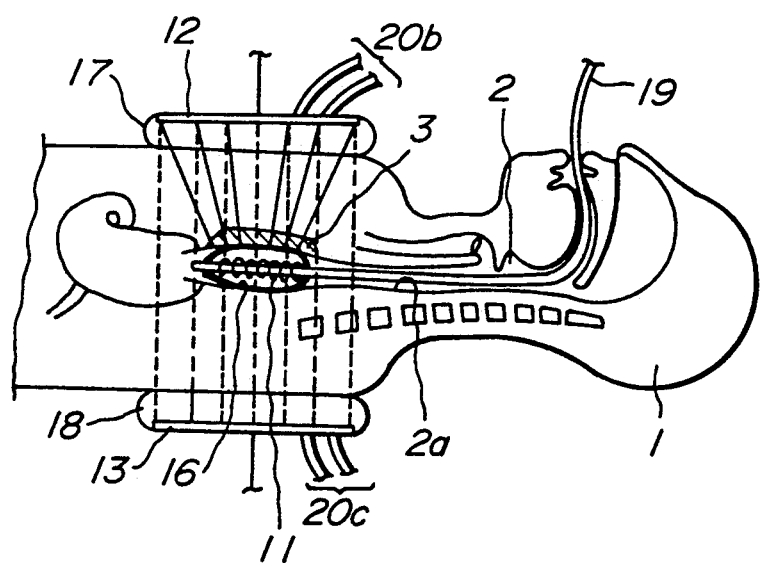
FIG. 4 is a schematic view explaining the heating operation with the aid of the apparatus shown in FIG. 3.

In the present embodiment, when the first and second electrodes 11 and 12 are selected, a restricted portion in the body 1 can be locally heated as shown by solid lines in FIG. 4, whilst when the second and third electrodes 12 and 13 are selected, a wider portion of the body is heated as illustrated by broken lines in FIG. 4. Therefore, the cancer 3 can be wholly heated substantially uniformly to a desired temperature at which the malignant tissues are selectively necrosed substantially regardless of the size and position of the cancer and any error in positioning the electrodes. Moreover, since the first pair of electrodes 11, 12 and the second pair of electrodes 12, 13 are alternately connected to the electric power supply device 15, the normal tissues can be effectively prevented from being heated excessively, and thus the hyperthermia apparatus can be continuously utilized for a long time period necessary for an optimum thermotherapy.

Figure 5:
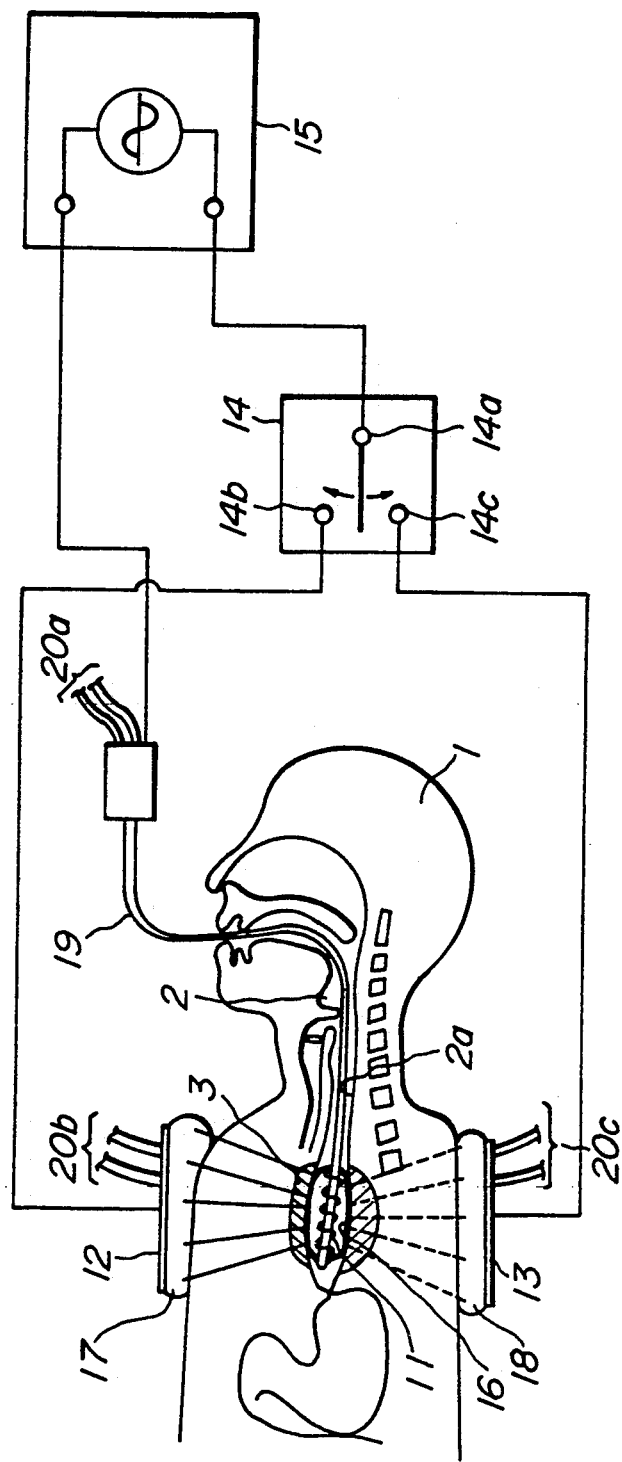
FIG. 5 is a schematic view showing the construction of another embodiment of the hyperthermia apparatus according to the invention.

FIG. 5 is a schematic view illustrating another embodiment of the hyperthermia apparatus according to the invention. In this embodiment, portions similar to those of the previous embodiment are denoted by the same reference numerals as those used in FIG. 3. The present embodiment differs from the previous embodiment only in the point that a first inside-body electrode 11 is directly connected to one output of an RF power supply device 15, and second and third outside-body electrodes 12 and 13 are connected to fixed contacts 14b and 14c of a switch 14, whose switching contact is connected to the other output of the power supply device 15. When a first pair of electrodes 11 and 12 is selectively connected to the power supply device 15, there is generated within a patient's body 1 an electric field illustrated by solid lines, while when a second pair of electrodes 11 and 13 are selected, an electric field shown by broken lines is generated across these electrodes.

In the present embodiment, since the first inside-body electrode 11 is always selected, the cancer 3 which is formed around the cavity 2 can be efficiently heated to a desired temperature. It should be noted that if cancers are existent in cavity wall portions opposing each other, it would be preferable to constitute a mode in which the second and third electrodes are selected.

As explained above, in the hyperthermia apparatus according to the invention, two electrodes including at least one outside-body electrode are selectively connected to the RF power supply device and the high frequency electric field is applied across the selected electrodes, so that the malignant tissues of the cancer can be wholly heated to the desired temperature, while the normal tissues can be effectively prevented from being heated to excessively high temperatures.

Figure 6:
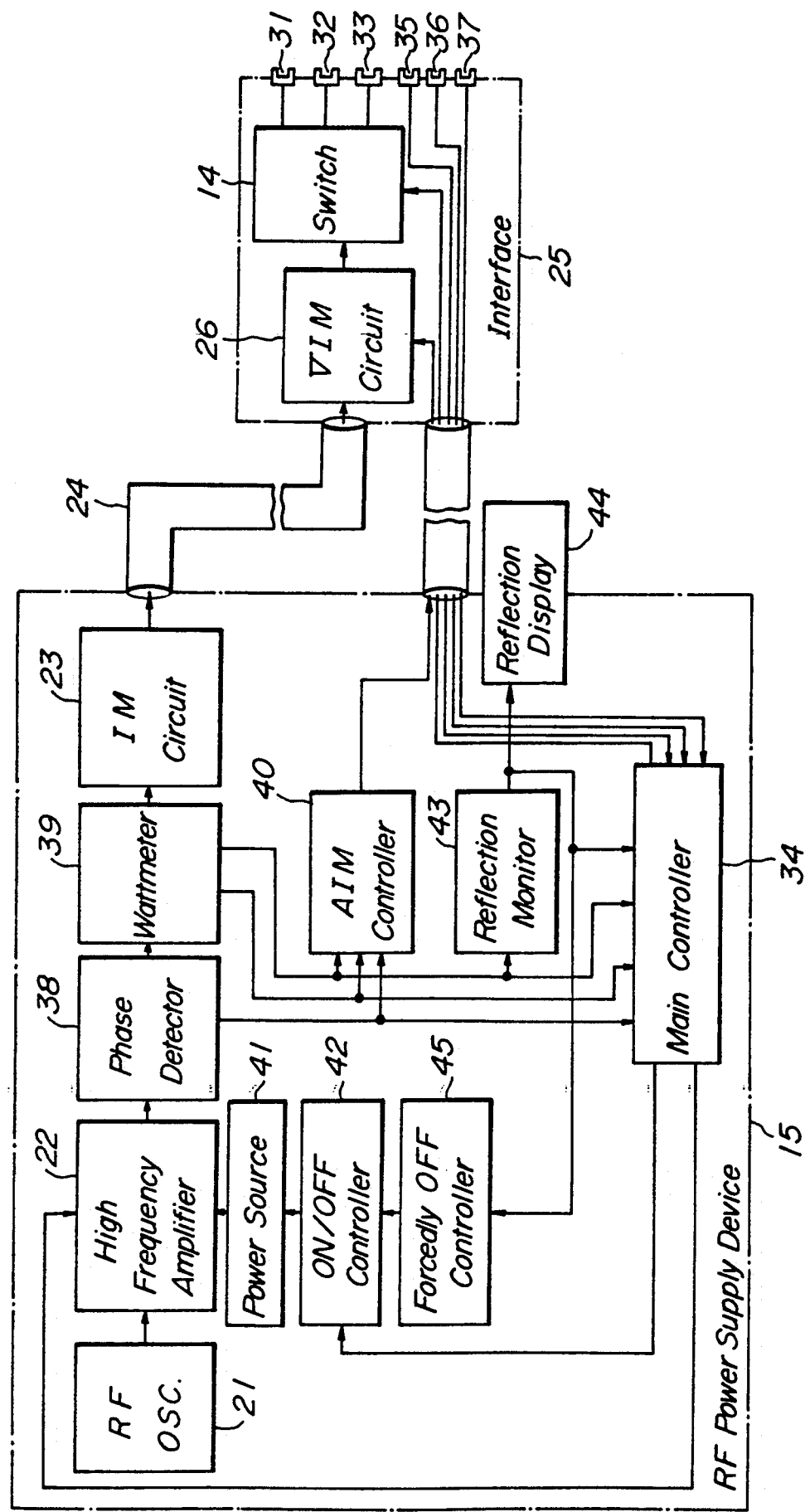
FIG. 6 is a circuit diagram depicting the detailed construction of an RF electric power generating device of the hyperthermia apparatus according to the invention.

FIG. 6 is a block diagram showing the detailed construction of an embodiment of the RF power supply device 15. In the present embodiment, an RF signal generated from an RF oscillator 21 is supplied via high frequency amplifier 22 and impedance matching (IM) circuit 23 to a co-axial cable 24. The impedance matching circuit 23 serves to attain the impedance matching with respect to the co-axial cable 24 and an output end of the co-axial cable is connected to an interface 25 which is arranged near the patient. The interface 25 comprises variable impedance matching (VIM) circuit 26, selection switch 14 and connectors 31, 32 and 33 to which connectors the first, second and third electrodes 11, 12 and 13 are connected via condutors, respectively. As explained above, two electrodes are selected among these three electrodes with the aid of the switch 14 and the RF power is supplied to the selected electrodes via the co-axial cable 24, variable impedance matching circuit 26 and switch 24. In the present embodiment, the electrode selecting operation of the switch 14 is controlled by a main controller 34 in accordance with a predetermined program. The interface 25 further comprises connectors 35, 36 and 37 to which temperature sensors arranged near respective electrodes 11, 12 and 13 are connected via conductors, respectively. Output signals supplied from the temperature sensors via the connectors 35, 36 and 37 are sent to the main controller 34. It should be noted that the switch 14 may be controlled in accordance with a program which uses the sensed temperatures as parameters.

Between the high frequency amplifier 22 and the impedance matching circuit 23, there are connected phase detector 38 for detecting a phase shift of the RF signal and wattmeter 39 of transmission type for measuring incident power and reflected power. Outputs of the phase detector 38 and wattmeter 39 are supplied to the main controller 34 as well as to an automatic impedance matching controller 40. This controller 40 supplies a control signal to the variable impedance matching circuit 26 such that the input impedance of the load circuit including two electrodes selected by the switch 14 is matched to the output impedance of the RF power supply device 15 including the co-axial cable 24.

The high frequency amplifier 22 is energized by a power source 41. The power source 41 is controlled by an ON/OFF controller 42 under the control of the main controller 34 such that the output power from the amplifier 22 is returned ON and OFF. For instance, when the electrodes are switched into or out of the circuit by the switch 14, the RF power is decreased to zero, and when the sensed temperatures increase or above decrease blow the predetermined values, the RF power is switched OFF or ON.

The reflected power measured by the wattmeter 39 is supplied also to an excessive reflection monitor 43. In the monitor 43, the measured reflection power is compared with a given freference value, and when the reflection power exceeds the reference value, a signal is supplied to an over-reflection display 44 to display the excessive reflection of the RF power. The monitor 43 supplies the signal also to the main controller 34 and a forcedly OFF controller 45, and the output power of the high frequency amplifier 22 is made OFF via the ON/OFF controller 42 and power source 41. Therefore, even if there occurs sudden impedance mismatching due to the disconnection of one or more electrodes from relevant connectors 31, 32 and 33, the excessive large reflection power which might damage the apparatus could never be produced.

Further, in the present embodiment, the amplification factor of the high frequency amplifier 22 is adjusted by the main controller 34 such that the output power of the amplifier 22 is decreased to a safe low level when the impedance matching becomes worse at a time of switching the electrodes and during the application of the RF power to the electrodes. Then, the automatic impedance matching is carried out at said safe low level, and after the impedance matching has been attained, the output power of the high frequency amplifier 22 is increased to the desired high level. In this manner, the apparatus can be protected against damage due to the impedance mismatching at the start time and during the application of the RF power to the electrodes, and at the same time, the patient is effectively prevented from being subjected to the dangerous electric shock.

In the above mentioned embodiment, after the output power of the high frequency amplifier 22 has been decreased to the lower level, the switching operation of electrodes is effected, but it is also possible to make the output power OFF from the low level or directly from the desired high level without interleaving the low level, and after the electrodes have been switched, the output power is slightly increased to the low level and the impedance matching is effected under this low level. Further, the switching of electrodes may be carried out manually instead of automatically. In this case, it is preferable to provide a manual switch for changing the output power of the high frequency amplifier 22 among the desired high level, safe low level and zero level, and prior to the selection of electrodes, the output power is manually set to the low level or zero level. After the selection of electrodes has been effected, the impedance matching is carried out automatically or manually under the low output power. When the impedance matching has been confirmed by an indicator such as meter, lamp or buzzer, the output power is increased to the high level by operating the manual switch. It should be noted that when using the manual selection switch 14, there may be provided a lock mechanism for inhibiting the operation of the switch as long as the high level power is generated from the high frequency amplifier 22. Moreover, there may be provided a photosensor or contact sensor for detecting the operation of the manual switch 14, and an alarm for producing an alarm sound or light when the switch is to be operated under the high output condition.

By utilizing the RF power supply device just explained above, the output power is switched into the low or zero level prior to the switching of electrodes, and after the electrodes have been switched, the impedance matching is carried out under the low level power and then the output power is increased to the high level for heating the body. Therefore, the apparatus is effectively protected against damage due to the impedance mismatching and further the patient can be prevented from being subjected to the electric shock, so that the thermotherapy can be performed safely.

In the embodiments so far explained, there are arranged one inside-body electrode and two outside-body electrodes, but the present invention is not restricted to such a construction. For instance, a plurality of inside-body electrodes may be inserted into the cavity of a patient's body extending in the longitudinal direction thereof and a corresponding number of outside-body electrodes may be arranged on the outer surface of the patient's body. Further, in the apparatus according to present invention the microwave power can be effectively used instead of the RF power.

Figure 7:
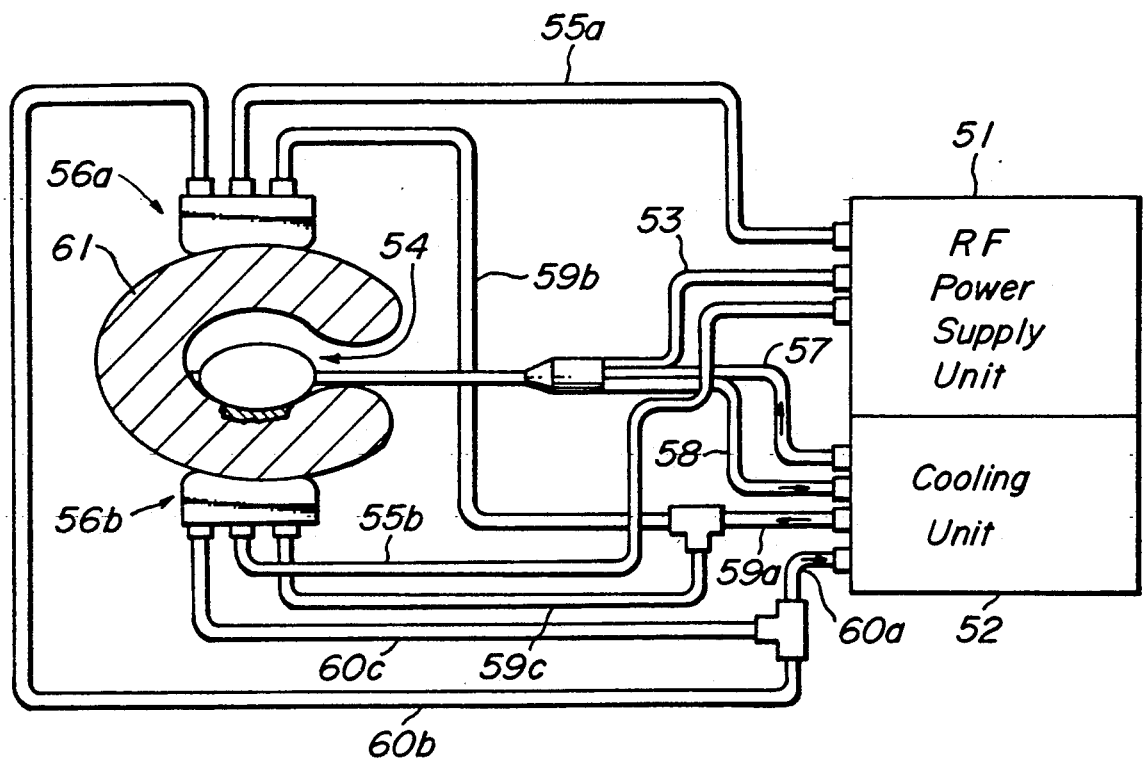
FIG. 7 is a schematic view illustrating the construction of another embodiment of the hyperthermia apparatus according to the invention.
Figure 8:
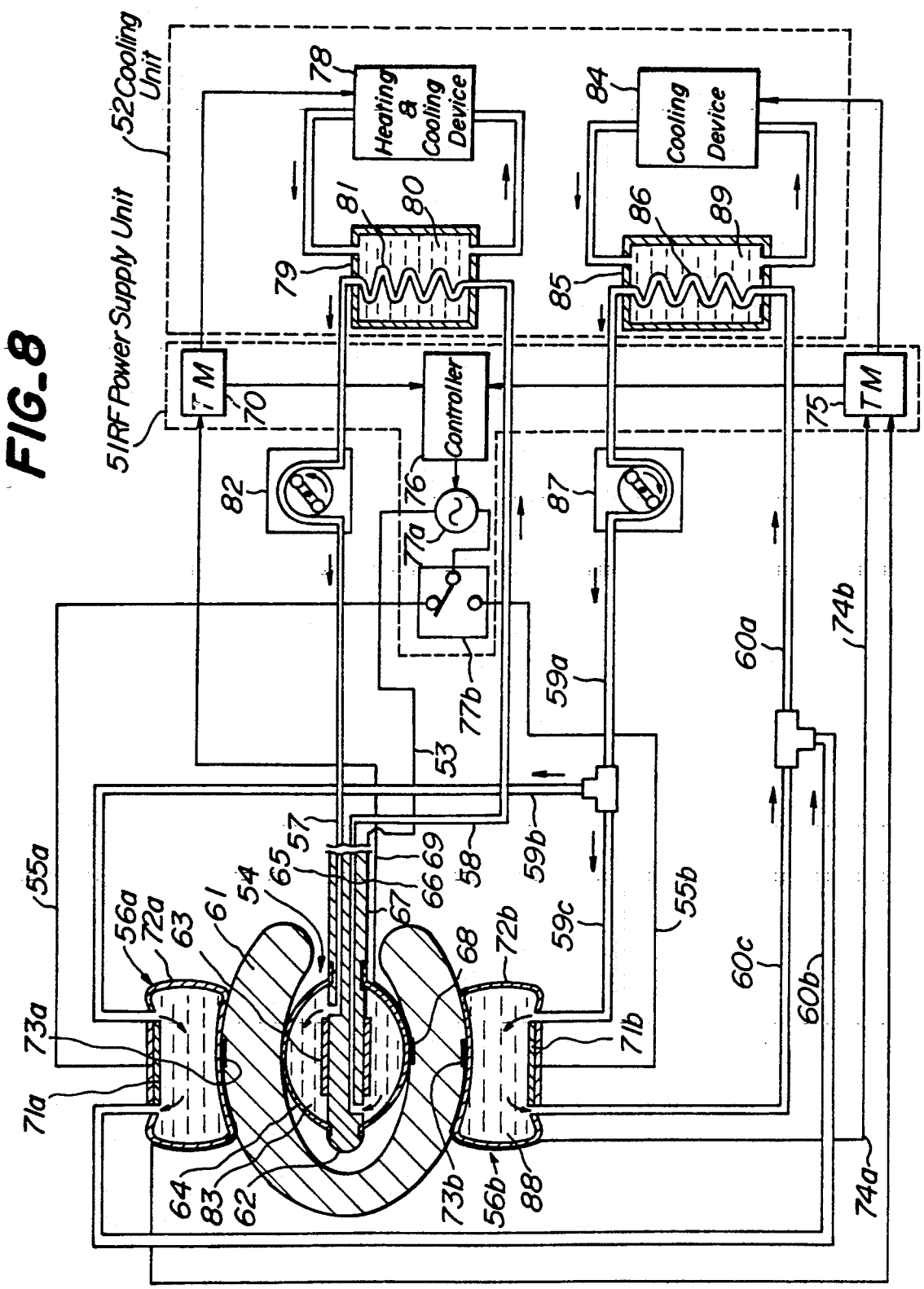
FIG. 8 is a schematic view showing the detailed construction of the apparatus shown in FIG. 7.

FIG. 7 is a schematic view illustrating the construction of another embodiment of the hyperthermia apparatus according to the invention, and FIG. 8 is a view showing its fluid system in detail. The hyperthermia apparatus comprises an RF supply unit 51 and a cooling unit 52. The RF power supply unit 51 is coupled with an electrode of an inside-body applicator 54 by means of an RF cable 53 as well as to electrodes of two outside-body applicators 56a and 56b via RF cables 55a and 55b, respectively. The cooling unit 52 is connected to a balloon of the inside-body applicator 54 through water supply and discharge pipes 57 and 58 as well as to balloons of the outside-body applicators 56a and 56b by means of water supply and discharge pipes 59a, 59b, 59c and 60a, 60b, 60c. The inside-body applicator 54 has a suitable size, shape and construction for easy insertion into the cavity of the body 61.

As illustrated in FIG. 8, the inside-body applicator 54 comprises a flexible rod 62 made of electrically insulating material, an inside-body electrode 63 arranged on a distal end of the rod and a balloon 64 made of electrically insulating material, the electrode being wholly surrounded by the balloon. In the rod 62 there are formed a duct 65 which is connected to the electrically insulating water supply pipe 57 and a duct 66 which is coupled with the water discharge pipe 58 made of electrically insulating material, these ducts being open within the balloon 64. On the outer surface of rod 62 there is applied a conductive strip 67 which is connected to the RF cable 53 and extends up to the electrode 63. On the outer surface of balloon 64 there is provided a thermocouple 68 which is connected via a conductor 69 to a temperature measuring device (TM) 70 arranged in the RF power supply unit 51.

The two outside-body applicators 56a and 56b have the same construction and comprise outside-body electrodes 71a and 71b connected the RF cables 55a and 55b, and balloons 72a, 72b made of electrically insulating material, the electrodes being separated from the body 61 by the balloons. To the balloon 72a are connected water supply and discharge pipes 59b and 60b, and to the balloon 72b are coupled water supply and discharge pipes 59c and 60c, said pipes being made of electrically insulating material. On the other surfaces of balloons 72a and 72b, there are provided thermocouples 73a and 73b which are connected via conductors 74a and 74b to a temperature measuring circuit 75 provided in the RF power supply unit 51. The temperature measuring circuits 70 and 75 detect temperatures at positions of the applicators 54, 56a and 56b, and supply signals to a power source controller 76 which then supplies a control signal to an RF signal source 77a. The output power of the RF signal generator 77a is supplied to electrodes via a selection switch 77b.

The cooling unit 52 comprises a heating/cooling device 78 and a heat exchanger 79 connected thereto, so that a liquid medium 80, for instance, water heated or cooled by the heating/cooling device is circulated through the heat exchanger 79. In the heat exchanger 79 there is arranged a coiled pipe 81 which is connected to the supply and discharge pipes 57 and 58. The coiled pipe 81 is made of electrically insulating material. In the supply pipe 57 is inserted a roller pump 82 for circulating an electrically conductive medium, i.e. saline solution 83 through pump 82—pipe 57—duct 65—balloon 64—duct 66—pipe 68—coiled pipe 81—pipe 57—pump 82. In the heat exchanger 79, the heat exchange is carried out between the water 80 and the medium 83 flowing through the coiled pipe 81, and thus the temperature of the medium 83 is controlled. It should be noted that the liquid medium 83 circulated through the balloon 64 of the inside-body applicator 54 serves not only to cool the living body, but also to heat the body. In the thermotherapy, it is necessary to heat the malignant tissues of cancer to a high temperature higher than 42° to 43° C. Therefore, during a start period of the thermotherapy, it is preferable to heat the body with the aid of the medium 83. In order to avoid the death or damage of normal tissues, it is necessary to keep the normal tissues at temperatures below 43° to 44° C., so that the medium 83 must have the function to cool the body. In this manner, the temperature of the medium 83 has to be controlled in accordance with temperatures of the part of the body at which the applicator 54 is arranged.

The outside-body applicators 56a and 56b must have the function for cooling the body, so that a cooling device 84 and a heat exchanger 85 coupled therewith are provided in the cooling unit 52. In the heat exchanger 85, there is arranged a coiled pipe 86 connected to the pipes 59a and 60a made of electrically insulating material. In the pipe 59a there is inserted a roller pump 87 for circulating a cooling medium 88 made of saline solution through pump 87—pipes 59a, 59b—balloon 72a—pipes 60b, 60a—coiled pipe 86—pipe 59a—pump 87 as well as pump 87—pipes 59a, 59c—balloon 72b—pipes 60c, 60a—coiled pipe 86—pipe 59—pump 87. The cooling device 84 is controlled by the temperature measuring circuit 75 to adjust the temperature of the saline solution 88.

In the present embodiment, the saline solutions 83 and 88 circulate through the balloons 64 and 72a, 72b and the waters 80 and 89 circulate via the heating/cooling devices 78 and 84 such that these devices are electrically isolated from each other, and therefore the saline solutions 83 and 88 are never short-circuited although the heating/cooling devices 78 and 84 are connected to the common power supply line. Further, the roller pumps 82 and 87 do not contact the saline solutions 83 and 88 and feed the solutions by squeezing the flexible tubes, so that although motors for rotating rollers of the roller pumps are commonly connected to the same power supply line, the solutions are not short-circuited at all through the roller pumps.

FIG. 9 is a partially cross sectional schematic view showing another embodiment of the cooling unit for controlling the temperature of the liquid mediums. This embodiment is applicable to the hyperthermia apparatus including two outside-body electrodes. In this embodiment, the cooling unit comprises a cooling device 84 and a heat exchanger 85 coupled therewith. In the heat exchanger 85, there are arranged two coiled pipes 86a and 86b, one being coupled with one outside-body applicator via pipes 90a, 91a and the other being connected to the other outside-body applicator by means of pipes 90b and 91b. In this manner, in the present embodiment, the saline solutions circulating through the outside-body applicator balloons can be completely isolated.

FIG. 10 shows another embodiment of the cooling unit according to the invention. In the present embodiment, a Peltier element 93 is provided on an outer surface of a housing of a heat exchanger 92 and temperature inside the housing is adjusted by supplying the electric power to the Peltier element. In the heat exchanger 92 is arranged a coiled pipe 94 which is communicated to the balloon of the applicator by means of pipes 95 and 96.

In the hyperthermia apparatus having the temperature controlling device explained above, the liquid mediums which are circulated through the balloons of the applicators are completely isolated from each other, and thus any accidental short-circuit can be effectively protected and the apparatus can be used safely. Further, the medium can be formed by the electrically conductive liquid such as the saline solution, it is possible to apply the high frequency field to the body efficiently and only the malignant tissues can be locally heated to the desired temperature.

Figure 11:
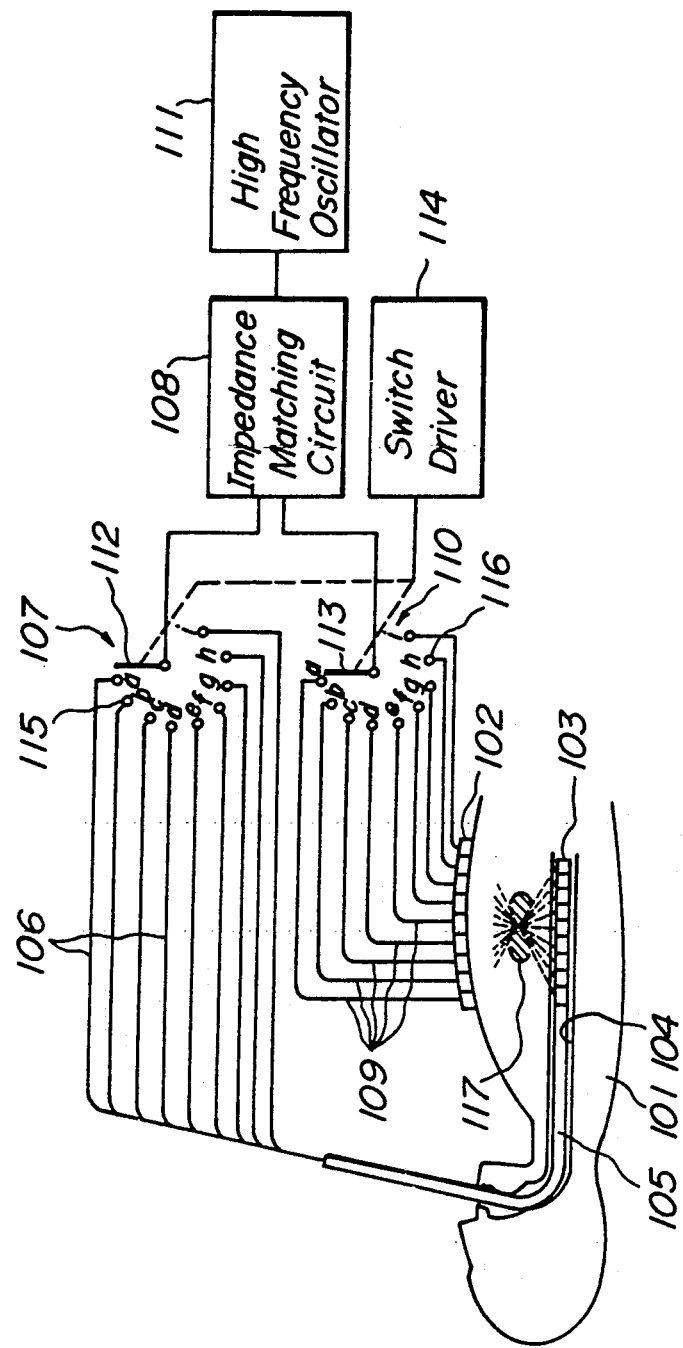
FIG. 11 is a schematic view illustrating still another embodiment of the hyperthermia apparatus according to the invention in which an electrode is divided into a plurality of sections.

FIG. 11 is a schematic view showing still another embodiment of the hyperthermia apparatus according to the invention. The apparatus comprises an outside-body electrode 102 arranged on an outer surface of a patient body 101, and an inside-body electrode 103 inserted into a cavity 104 of the body 101. The inside-body electrode 103 is arranged at a distal end of a flexible insertion member 105 which can be easily inserted into the cavity 104 of the body. The electrodes 102 and 103 are divided into a corresponding number of electrode sections a~i which are arranged along lines. That is to say, the electrode sections a~i of the inside-body electrode 103 are aligned in the longitudinal direction of the insertion member 105.

To each electrode sections of the inside-body electrode 103 are connected respective conductors 106 which are connected to selection contacts 115 (a~i) of a first rotary switch 107 whose switching arm 112 is connected to an impedance matching circuit 108. Similarly, each electrode section of the outside-body electrode 102 is connected via conductors 109 to respective selection contacts 116 (a~i) of a second rotary switch 110 whose switching arm 113 is also connected to the impedance matching circuit 108. The impedance matching circuit 108 is connected to a high frequency oscillator 117. The switching arms 112 and 113 of the first and second rotary switches 107 and 110 are rotated by a switch driver 114 in conjunction with each other at a given speed. Therefore, the corresponding electrode sections a~i of the electrodes 102 and 103 are successively energized with the high frequency power supplied from the oscillator 111 at a given repetition period.

Now the manner of using the above mentioned hyperthermia apparatus will be explained. At first, the insertion member 105 is inserted into the cavity 104 of the body 101 such that the inside-body electrode 103 is positioned to face to a cancer 117. Then, the outside-body electrode 102 is arranged and fixed on the outer surface of the body 101 such that the cancer is sandwiched between the electrodes 102 and 103. That is to say, the electrode sections a~i of the outside-body electrode 102 are faced to corresponding electrode sections a~i of the inside-body electrode 103 in a symmetrical manner, while the center point of symmetry is positioned at a center of the cancer 117.

Next, the switching arms 112 and 113 of the first and second rotary switches 107 and 110 are rotated in conjunction with each other by means of the switch driver 114 so that corresponding switching contacts a~i are successively connected to the switching arms at the constant period. In this manner, a first pair of electrode sections a, a; a second pair of electrode sections b, b; a third pair of electrode sections c, c; . . . of the outside-body and inside-body electrodes 102 and 103 are successively energized with the high frequency power supplied from the high frequency oscillator 111. Therefore, across electrode sections of successive pairs are generated the high frequency electric fields as shown by broken lines in FIG. 11, and the cancer 117 is locally heated to a desired high temperature. That is to say, in the present embodiment, portions of the body 101 near the electrodes 102 and 103 are not continuously subjected to the strong electric field so that these portions are not heated to higher temperatures, while the cancer 117 is always exposed to the electric fields and is heated to the high temperature. Therefore, it is no longer necessary to provide a larger cooling unit for cooling the electrode sections, so that the electrode sections a~i can be simple in construction and small in size. Further, the inside-body electrode 103 to be inserted into the cavity 104 of the body 101 can be made very small and the patient can be protected from pain.

FIG. 12 is a schematic view illustrating still another embodiment of the hyperthermia apparatus according to the invention. Similar to the previous embodiment illustrated in FIG. 12, an outside-body electrode 102 is divided into a plurality of electrode sections a~i, but an inside-body electrode 125 is arranged movably in an insertion member 105 in its longitudinal direction. In the insertion member 105 is also inserted a wire 126 whose one end is connected to the inside-body electrode 125. The other end of the wire 126 is wound around a pulley 127 which is connected to a stepping motor 128.

To respective electrode sections a~i of the outside-body electrode 102 are connected via respective conductors 129 to switching contacts of a rotary switch 130 whose switching arm 132 is connected to a high frequency oscillator 131. The switching arm 132 of the rotary switch 130 is coupled with a second stepping motor 133. The first and second stepping motors 128 and 133 are driven by a motor driver 134 in conjunction with each other. It should be noted that the wire 136 inserted into the insertion member 105 serves also as an electric conductor for supplying the high frequency power from the oscillator 131 to the inside-body electrode 125.

In the present embodiment, the high frequency power from the oscillator 131 is supplied by means of the wire 126 and rotary switch 130 to the outside-body electrode 102 and inside-body electrode 125. To each electrode section a~i of the outside-body electrode 102 the high frequency power is successively supplied for a given period by means of the rotary switch 130 which is driven by the second stepping motor 133. In synchronism therewith, the pulley 127 is rotated by the first stepping motor 128 to wind or rewind the wire 126, so that the inside-body electrode 125 is moved along the insertion member 105 in such a manner that lines connecting the inside-body electrode 125 and successively energized electrode sections a~i of the outside-body electrode 102 cross each other at a point within the cancer 117 of the patient 101. Therefore, the high frequency electric field is always applied to the cancer 117 and the cancer is locally heated to the desired temperature, while temperatures of portions of the body near the electrodes can be effectively prevented from being heated excessively. In the manner explained above, the single inside-body electrode 125 is moved such that it situates at positions which are point-symmetrical with respect to the electrode sections a~i of the outside-body electrode 102, and thus the single inside-body electrode 125 serves substantially as a plurality of electrode sections.

In the embodiments shown in FIGS. 11 and 12, the outside-body electrode is divided into a plurality of electrode sections and the inside-body electrode is also divided into a plurality of electrode-sections or is moved along the insertion member, and the high frequency power is supplied across the successive electrode sections of the outside-body electrode and inside-body electrode or across the successive electrode sections of the outside-body electrode and the movable inside-body electrode such that the high frequency electric fields are concentrated at the cancer, and therefore the malignant tissues can be locally heated to the desired high temperature.

In the embodiments so far explained, the electric power of high frequency is selectively supplied to two electrodes by means of the two contact switches and rotary switch, but according to the invention, the electrode selecting means may be constructed by semiconductor switches. Further, there may be arranged a plurality of high frequency power supply sources each corresponding to respective electrodes and the operation of these power supply sources may be switched. Moreover, in the embodiment illustrated in FIG. 11, the number of electrode sections of the inside-body electrode may be smaller than that of the outside-body electrode.

What is claimed is:

1. A hyperthermia apparatus, comprising:
   at least two outside-body electrodes;
   at least one inside-body electrode which is insertable into a cavity of a living body;
   power source means for supplying high frequency electric power across two selected electrodes, including one of said two outside-body electrodes, to heat a portion of the living body interposed between said two selected electrodes to a desired temperature, said power source means comprising a high frequency power supply circuit with two output terminals, one of said output terminals being connected to a selected one of said two outside-body electrodes; and
   selection means for selecting said two selected electrodes, said selection means comprising a switch having a common switching contact connected to the other one of said output terminals and two fixed contacts, one of said two fixed contacts being connected to said inside-body electrode and the other one of said two fixed contacts being connected to the non-selected one of said two outside-body electrodes.

2. The hyperthermia apparatus of claim 1, wherein said power source means further comprises: a variable impedance matching circuit connected between said high frequency power supply circuit and said switch of said selection means; and a control circuit comprising means for changing an output power of said high frequency power supply circuit to a low level prior to switching electrodes and increasing the output level of said high frequency power supply circuit to a desired high level after the impedance matching has been attained under said low level.

3. The hyperthermia apparatus of claim 2, wherein said control circuit changing means controls said output power such that a level of the output power of said high frequency power supply circuit is set to said low level prior to initiating the power supply to electrodes and is increased to said high level after the impedance matching has been attained by said impedance matching circuit.

4. The hyperthermia apparatus of claim 2, wherein said impedance matching circuit comprises an automatic impedance matching circuit.

5. A hyperthermia apparatus, comprising:
   at least two outside-body electrodes, at least one of said outside-body electrodes being divided into a plurality of electrode sections;
   at least one inside-body electrode which is insertable into a cavity of a living body;
   selection means for selecting two electrodes including at least one of said outside-body electrodes, said selection means comprising a switch for supplying high frequency electric power successively to said electrode sections during a given period; and
   power source means for supplying said high frequency electric power across said two electrodes selected by said selection means to heat a portion of the living body interposed between said two electrodes to a desired temperature.

6. The hyperthermia apparatus of claim 5, wherein said inside-body electrode is arranged movably in an insertion member to be inserted into a cavity of the living body, the apparatus further comprising means for moving said inside-body electrode.

7. A hyperthermia apparatus, comprising:
   two outside-body electrodes each comprising a balloon which surrounds each of said two outside-body electrodes and separates each of said two outside-body electrodes from a living body;
   one inside-body electrode which is insertable into a cavity of the living body, said inside body electrode comprising a balloon which surrounds said inside body electrode and separates said inside-body electrode from the living body;
   means for circulating liquid mediums having controlled temperatures through said balloon of said inside-body electrode and each said balloon of said two outside-body electrodes;
   power source means for supplying high frequency electric power across two selected electrodes including one of said two outside-body electrodes to heat a portion of the living body interposed between said two selected electrodes to a desired temperature, said power source means comprising a high frequency power supply circuit with two output terminals, one of said output terminals being connected to the selected one of said two outside-body electrodes; and
   selection means for selecting said two selected electrodes, said selection means comprising a switch having a common switching contact connected to the other one of said output terminals and said two fixed contacts, one of said two fixed contacts being connected to said inside-body electrode and the other one of said two fixed contacts being connected to the non-selected one of said two outside-body electrodes.

8. The hyperthermia apparatus of claim 7, wherein said means for circulating liquid mediums comprises a first means for circulating a first medium through said balloon of said inside-body electrode and a second means for circulating a second medium through each said balloon of said two outside-body electrodes.

9. The hyperthermia apparatus of claim 8, wherein said first circulating means comprises a first liquid path coupled with said balloon of said inside-body electrode, a first pump and a first heat exchanger inserted in said first liquid path, and a first heating/cooling device communicating with said first heat exchanger for circulating a first temperature controlled fluid through said first heat exchanger, and said second circulating means comprises a second liquid path coupled with each said balloon of said two outside-body electrodes, a second pump and a second heat exchanger inserted in said liquid path, and a second heating/cooling device communicating with said second heat exchanger for circulating a second temperature controlled fluid through said second heat exchanger.

10. The hyperthermia apparatus of claim 8, wherein said first circulating means comprises a first liquid path coupled with said balloon of said inside-body electrode, a first pump and a first heat exchanger inserted in said first liquid path, and a first heating/cooling device provide in communication with said first heat exchanger for circulating a first temperature controlled fluid through said first heat exchanger, and said second circulating means comprises a second liquid path coupled with one of each said balloon of said two outside-body electrodes, a second pump and a first coiled pipe inserted in said second liquid path, a third liquid path coupled with the other of each said balloon of said two outside-body electrodes, a third pump and a second coiled pipe inserted in said third liquid path, a second heat exchanger inserted in said second liquid path for accommodating said first and second coiled pipes, and a second cooling device provided in communication with said second heat exchanger for circulating a temperature controlled fluid through said second heat exchanger.

11. A hyperthermia apparatus, comprising:
two outside-body electrodes;
one inside-body electrode which is insertable into a cavity of a living body;
power source means for supplying high frequency electric power across two selected electrodes, including one of said two outside-body electrodes, to heat a portion of the living body interposed between said two selected electrodes to a desired temperature; said power source means comprising a high frequency power supply circuit with two output terminals, one of the output terminals being connected to said one inside-body electrode; and
selection means for selecting said two selected electrodes, said selection means comprising a switch having a common switching contact connected to the other one of said output terminals and two fixed contacts, whereihn said two outside-body electrodes are connected to said two fixed contacts.

* * * * *